United States Patent [19]

Rohr et al.

[11] Patent Number: 5,383,938
[45] Date of Patent: Jan. 24, 1995

[54] LOCKING RING FOR AN ACETABULAR CUP

[75] Inventors: William Rohr, Warsaw; Melissa Broderick, North Webster; Tony Gonzalez, Winona Lake, all of Ind.

[73] Assignee: Zimmer, Inc., Warsaw, Ind.

[21] Appl. No.: 158,471

[22] Filed: Nov. 29, 1993

Related U.S. Application Data

[63] Continuation of Ser. No. 17,112, Feb. 12, 1993, abandoned.

[51] Int. Cl.$^6$ ............................................. A61F 2/34
[52] U.S. Cl. .................................... 623/22; 623/18
[58] Field of Search .................... 623/16, 18, 19, 20, 623/22, 23; 411/353, 517, 518; 285/365, 407

[56] References Cited

U.S. PATENT DOCUMENTS

| | | | |
|---|---|---|---|
| 1,758,515 | 5/1930 | Heiermann | 411/517 |
| 2,382,947 | 8/1945 | Brozek | 411/518 |
| 2,544,631 | 3/1951 | Heimann et al. | 411/518 |
| 2,595,787 | 5/1952 | Heimann | 287/53 |
| 2,873,586 | 2/1959 | Krandall | 411/517 |
| 3,104,905 | 9/1963 | Erdmann et al. | 411/517 |
| 3,412,774 | 11/1968 | Schuster | 411/353 |
| 3,701,303 | 10/1972 | Kondo | 411/518 |
| 3,906,550 | 9/1975 | Rostoker et al. | 3/1.912 |
| 4,380,090 | 4/1983 | Ramos | 3/1.912 |
| 4,619,658 | 10/1986 | Pappas et al. | 623/22 |
| 4,676,798 | 6/1987 | Noiles | 623/22 |
| 4,687,399 | 8/1987 | Petrie | 411/518 |
| 4,765,033 | 8/1988 | Hollingsworth | 411/517 |
| 4,770,661 | 9/1988 | Oh | 623/22 |
| 4,798,610 | 1/1989 | Averill et al. | 623/22 |
| 4,881,860 | 11/1989 | Kanazawa | 411/353 |
| 4,883,490 | 11/1989 | Oh | 623/22 |
| 4,908,033 | 3/1990 | Frey et al. | 623/22 |
| 4,936,855 | 6/1990 | Sherman | 623/22 |
| 4,960,427 | 10/1990 | Noiles | 623/22 |
| 4,987,650 | 1/1991 | Eickmann | 411/517 |
| 5,002,580 | 3/1991 | Noble et al. | 623/23 |
| 5,004,475 | 4/1991 | Vermeire | 623/23 |
| 5,019,105 | 5/1991 | Wiley | 623/22 |
| 5,049,158 | 9/1991 | Engelhardt et al. | 623/22 |
| 5,080,678 | 1/1992 | Spotorno et al. | 623/22 |
| 5,171,285 | 12/1992 | Broderick | 623/22 |
| 5,195,860 | 3/1993 | Steyn | 411/353 |

FOREIGN PATENT DOCUMENTS

| | | |
|---|---|---|
| 0019361 | 11/1980 | European Pat. Off. . |
| 262051 | 9/1949 | Switzerland . |
| WO92/09815 | 6/1992 | WIPO . |

*Primary Examiner*—David Isabella
*Attorney, Agent, or Firm*—Todd A. Dawson

[57] ABSTRACT

The metal lock ring of the invention has an oblong exterior periphery which allows the ring to have a small "width" and a larger "height." The small "width" provides a strong locking mechanism on the poly liner and the larger "height" allows the ring to remain secure within the groove of the metal shell prior to and during assembly of the polyethylene liner. The ring has a chamfer on its inside leading edges defining its width to facilitate assembly of the liner. This optimizes the ease of assembly and is simpler and more economically to produce than a chamfer all the way around the oblong ring. In the preferred embodiment, the lock ring has a constant thickness such that the inner periphery and the outer periphery are oval.

In an alternative embodiment, the metal lock ring has a round inner diameter and a round outer diameter that are not concentric, thereby creating a thickening of the ring at one end. The shape of the alternative lock ring provides for substantial contact between the lock ring and the poly liner about the liner. The thickened area of the ring retains the ring within the metal cup prior to and during assembly of the poly liner. The thickened portion of the ring may have scallops or notches formed therein to increase the flexibility of the ring.

3 Claims, 3 Drawing Sheets

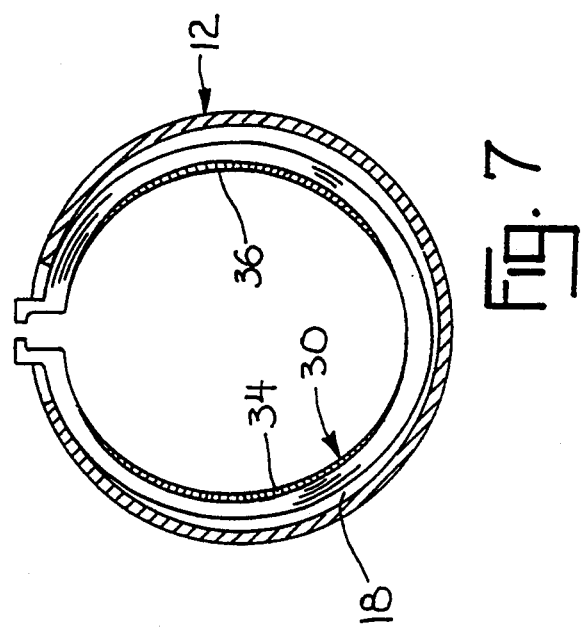
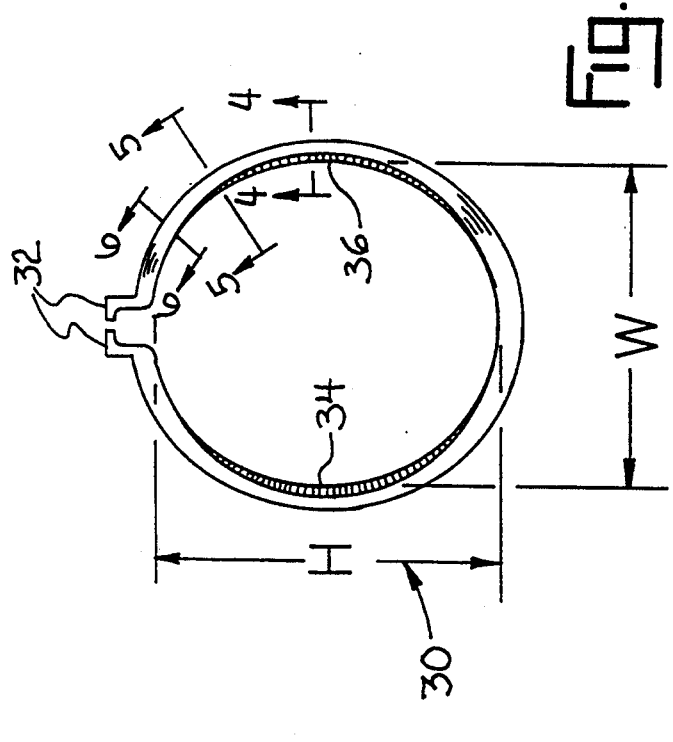
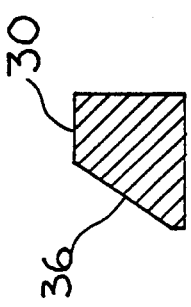
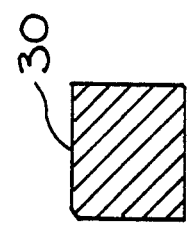
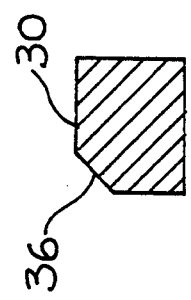

LOCKING RING FOR AN ACETABULAR CUP

This application is a continuation of application Ser. No. 08/017,112 filed Feb. 12, 1993, now abandoned.

FIELD OF THE INVENTION

This invention relates to acetabular cup assemblies having a cup and a liner retained in the cup by a locking ring for use in total hip arthroplasty and has specific relevance to a locking ring for retaining a poller liner within a metal cup.

BACKGROUND OF THE INVENTION

Prosthetic acetabular cups are well known in the industry for replacing a portion of a patient's hip joint during total hip arthroplasty. One form of acetabular component includes a metal cup and a polyethylene liner secured therein by a variety of mechanical fasteners. The metal cup is affixed to the prepared acetabulum either by mechanical fasteners or by cement. Some metal cups include a porous surface layer to provide a structure for bone growth to enhance fixation of the cup. The polyethylene liner forms the articular surface for mating with the head of the femur or implant and are connected to the metal cup by a variety of fastening devices.

Once such device for retaining the liner within the cup is a round lock ring which is carried within a groove formed in the metal cup and communicates in an interference fit with a groove formed on the exterior of the polyethylene liner. This type of cup assembly is generally packaged with the lock ring and metal cup connected and the liner packaged separately. During the surgery, the liner is placed into the metal cup by pressing the liner into the cup and thereby spreading the lock ring slightly. The lock ring snaps into the groove formed on the exterior of the liner when properly aligned. The lock ring has a generally constant diameter or, in other words, is circular.

A problem exists with this type of construction since the lock ring is free floating within the groove of the metal cup prior to insertion of the liner. As the ring floats to one side, the other side of the ring is no longer supported by the metal shell. This can result in disassembly of the ring or difficult assembly of the poly liner.

SUMMARY OF THE INVENTION

The metal lock ring of the invention has oblong exterior periphery which allows the ring to have a small "width" and a larger "height." The small "width" provides a strong locking mechanism on the poly liner and the larger "height" allows the ring to remain secure within the groove of the metal shell prior to and during assembly of the polyethylene liner. The ring has a chamfer on its inside leading edges defining its width to facilitate assembly of the liner. The chamfer is produced on the ring so that there is a maximum chamfer at the "width" and little or no chamfer at the "height." This optimizes the ease of assembly and is simpler and more economical to produce than a chamfer all the way around the oblong ring. In the preferred embodiment, the lock ring has a constant thickness such that the inner periphery and the outer periphery are oval.

In an alternative embodiment, the metal lock ring has a round inner diameter and a round outer diameter that are not concentric, thereby creating a thickening of the ring at one end. The shape of the alternative lock ring provides for substantial contact between the lock ring and the poly liner about the liner. The thickened area of the ring retains the ring within the metal cup prior to and during assembly of the poly liner. The thickened portion of the ring may have scallops or notches formed therein to increase the flexibility of the ring.

Accordingly, it is an advantage of the invention to provide for a novel lock ring for an acetabular cup.

Another advantage of the invention is to provide for a locking ring for an acetabular cup which is retained within the groove of the metal shell prior to and during insertion of the polyethylene liner.

Another advantage of the invention is to provide for a locking ring for an acetabular cup which has an oblong external periphery having a width smaller than the length.

Another advantage of the invention is to provide for a locking ring for an acetabular cup which has an oblong external periphery having a width smaller than the length and which includes beveled edges along the width.

Still another advantage of the invention is to provide a locking ring having a thickened area for retaining the ring within the groove of the acetabular component prior to and during assembly of the polyethylene liner.

Another advantage of the invention is to provide a locking ring for an acetabular assembly wherein the external periphery and the internal periphery define non-concentric circles relative to one another.

Other advantages of the invention will become apparent upon a reading of the following description taken with the accompanying drawings.

BRIEF DESCRIPTION OF THE DRAWINGS

FIG. 3 is an elevational view of the locking ring of the invention having a width "W" and a height "H."

FIG. 4 is a cross sectional view taken along line 4—4 of FIG. 3.

FIG. 5 is a cross sectional view taken along line 5—5 of FIG. 3.

FIG. 6 is a cross sectional view taken along line 6—6 of FIG. 3.

FIG. 7 is an elevational view with portions sectioned for illustrative purposes showing the lock ring of FIGS. 3–6 carried within a metal cup.

DESCRIPTION OF THE PREFERRED EMBODIMENTS

The preferred embodiments herein described are not intended to be exhaustive or to limit the invention to the precise forms disclosed. Rather, they are chosen and described to best explain the invention so that others skilled in the art might utilize their teachings.

Figure 2:
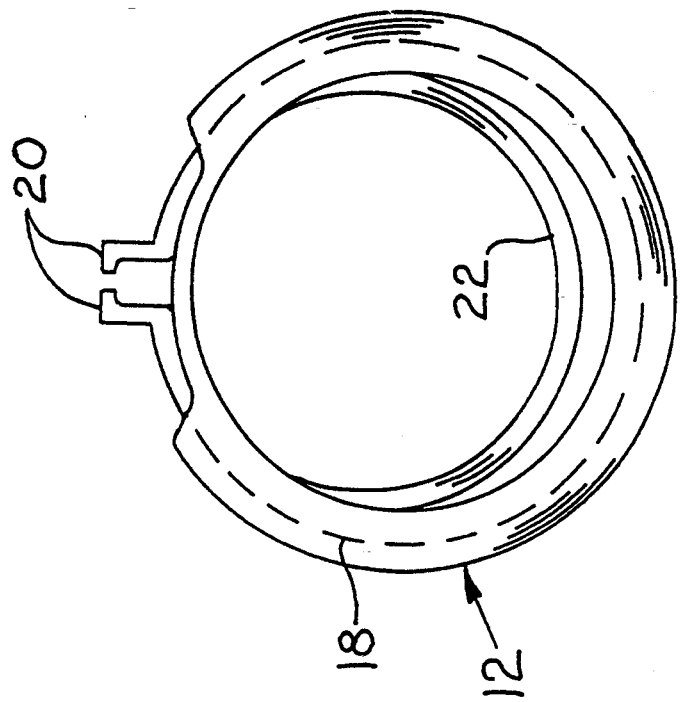
FIG. 2 is a elevational view illustrating the prior art metal cup and the prior art lock ring with the lock ring positioned such that a portion is unsupported by the metal cup.
Figure 1:
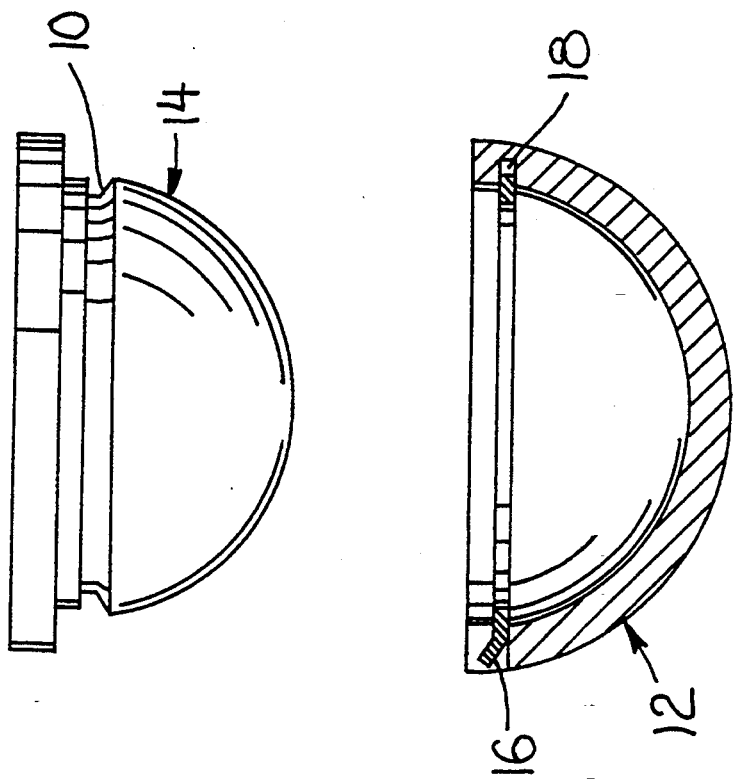
FIG. 1 is a sectional view of a polyethylene liner positioned for insertion into a prior art metal cup and lock ring.

FIGS. 1 and 2 illustrate a prior art acetabular cup assembly as including a metal cup 12, a polyethylene liner 14 and a round metal locking ring 16. Metal cup 12 defines a generally hemispherical cavity for accommodating the polyethylene liner in a known manner. An annular groove 18 is formed in metal cup 12. A portion of the metal cup adjacent the annular groove is removed to expose the groove for accommodation of the metal ring 16. Metal ring 16 is round and of a constant cross section about a substantial portion of the ring. As illustrated, ring 16 is interrupted and a pair of legs 20 are formed. Legs 20 form a means for connection of a removal device to spread the ring and permit the liner to be removed from the cup. Liner 14 includes an annular groove 10. In use, the ring extends inwardly a small amount from the edge of the metal cup 12 such that as the liner 14 is press into the metal cup 12, the liner engages the ring and spreads it slightly. When the annular groove 10 formed about the liner is aligned with the locking ring 16, the ring springs into the groove in an interference fashion to retain the liner within the cup.

FIG. 2 illustrates the problem with prior art locking rings. As illustrated, the ring 16 is shifted within groove 18 so that a portion 22 of the ring 16 is unsupported. If inverted with the ring in this position, the ring could fall out or become wedged in an undesirable position. Further with the ring in this position, the liner is more difficult to insert.

FIG. 3 illustrates the lock ring 30 of the invention for use with the prior art metal cup and polyethylene liner. Lock ring 30 has a generally oblong internal and external periphery having a width "W" and a height "H." Width W is less than height H. The internal edges 33, 34 defining the width of locking ring are chamfered as illustrated. The chamfer on edges 33, 34 is at a maximum at the minimum width and tapers toward the height. FIGS. 3 through 6 illustrate the varying chamfer of ring 30. As with the prior art ring, ring 30 is interrupted and includes a pair of legs 32 extending from the interruption and constitutes a connection mechanism for a spreading tool for removal of the poly liner.

FIG. 7 illustrates the lock ring 30 carried by metal cup 12 within groove 18 of the cup. It should be noted that the oblong configuration of ring 30 prevents the ring from being shifting into an unsupported position as illustrated with the prior art ring of FIG. 2. It should be noted that in use with an polyethylene liner of the type illustrated in FIG. 1, only the sides 34, 36 of the ring will seat within the groove 10 of the liner.

Figure 8:
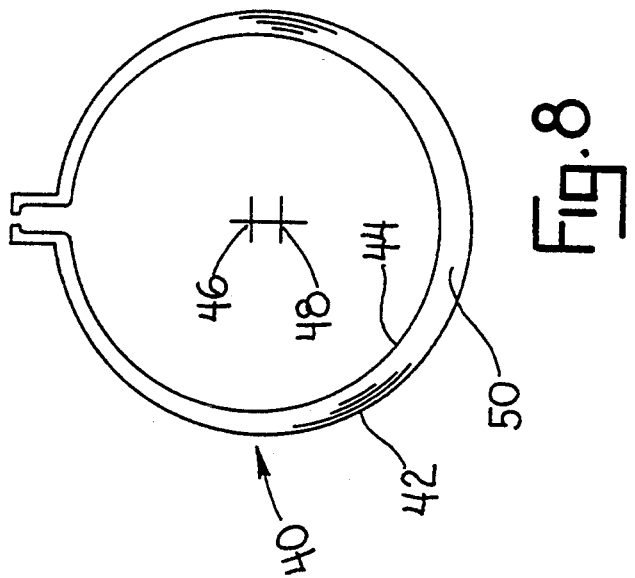
FIG. 8 is an elevational view of a second embodiment of the lock ring of the invention.

FIG. 8 illustrates a second embodiment of the invention wherein a lock ring 40 includes a circular external periphery 42 and a internal circular periphery 44. The center 46 of the external periphery 42 and the center 48 of the internal periphery 44 are shifted relative to one another or in other words are in a non-concentric relationship. This non-concentric orientation forms a lock ring 40 having a thickened portion 50. Ring 40 is configured to be accommodated by groove 18 of metal cup 12 such that the thickened portion 50 prevents the ring from shifting into an unsupported position as illustrated with the prior art lock ring of FIGS. 1 and 2.

Figure 10:
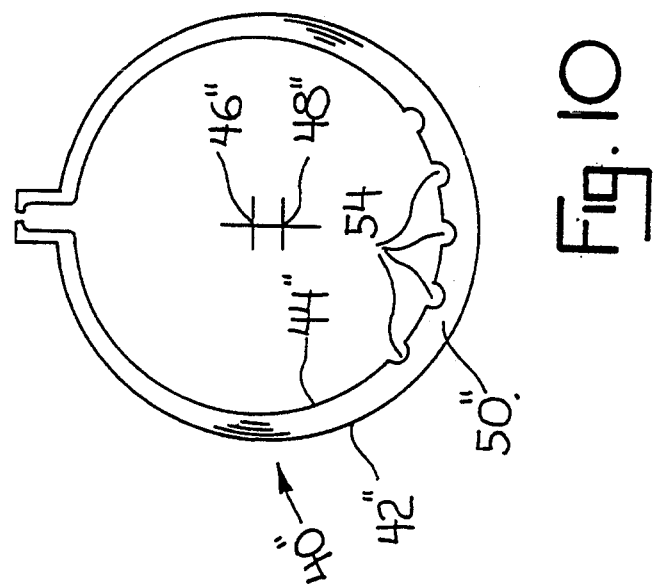
FIGS. 9 and 10 are elevational views of an alternative design of the second embodiment of FIG. 8.
Figure 9:
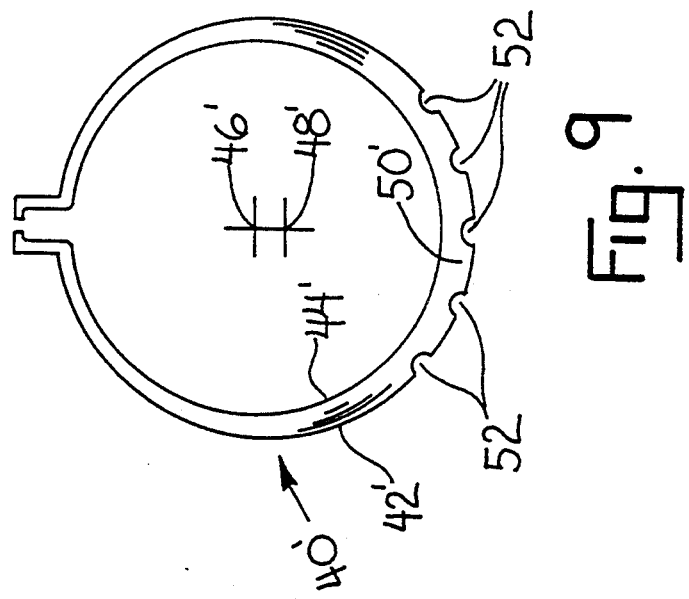

FIGS. 9 and 10 illustrate alternative embodiments 40' and 40" of the lock ring 40. To increase flexibility of lock ring 40', a plurality of scallops or notches 52 are formed in the external periphery 42' at the thickened portion 50' (see FIG. 9). In FIG. 10, the lock ring 40" includes a plurality of scallops or notches 54 formed in the internal periphery 44" at the thickened section 50" to increase flexibility of the lock ring.

It should be understood that the invention is not to be limited to the precise forms disclosed but may be modified within the keeping of the appended claims.

We claim:

1. In combination, a prosthetic acetabular cup and a locking ring for removably retaining an acetabular liner within the cup, the acetabular cup defining an opening for accommodating the liner, an annular groove being formed in said cup adjacent the opening, the locking ring being partially supported within the annular groove, the locking ring having an interior periphery and an exterior periphery cooperating to define a means for preventing the ring from disengaging with the cup prior to insertion of the liner, wherein said locking ring is oblong such that at least two opposed points of the locking ring remain supported by the cup when the locking ring is shifted relative to the cup.

2. The combination of claim 1 wherein said ring is formed having a generally constant cross section.

3. The combination of claim 2 wherein the ring defines a length and a width in generally transverse planes, wherein said width is less than said length.

* * * * *